United States Patent [19]

Loren et al.

[11] Patent Number: 4,564,803
[45] Date of Patent: Jan. 14, 1986

[54] METHOD AND APPARATUS FOR REMOVING FOREIGN MATTER FROM A FLOW CELL OF A PARTICLE STUDY DEVICE

[75] Inventors: Mark Loren, Miami Beach; Raul I. Pedroso, Miami, both of Fla.

[73] Assignee: Coulter Corporation, Hialeah, Fla.

[21] Appl. No.: 527,455

[22] Filed: Aug. 29, 1983

[51] Int. Cl.⁴ ............................................ G01N 27/00
[52] U.S. Cl. ..................................... 324/71.1; 134/36
[58] Field of Search .............. 324/71.1, 71.4; 377/10, 377/11, 12; 364/555; 134/36, 37; 356/39

[56] References Cited

U.S. PATENT DOCUMENTS

| | | | |
|---|---|---|---|
| 3,259,891 | 7/1966 | Coulter et al. | 324/71.1 |
| 3,266,934 | 8/1966 | Alexander | 134/36 |
| 3,648,158 | 3/1972 | Parker | 324/71.1 |
| 3,710,933 | 1/1973 | Fulwyler et al. | 356/39 |
| 3,752,170 | 8/1973 | Murbach | 134/37 |
| 3,781,675 | 12/1973 | Angel | 324/71.1 |
| 3,854,088 | 10/1974 | Gahwiler | 324/71.1 |
| 3,963,984 | 6/1976 | Coulter | 324/71.1 |
| 4,070,617 | 1/1978 | Kachel et al. | 324/71.1 |
| 4,157,498 | 6/1979 | Johnson | 324/71.1 |
| 4,419,141 | 12/1983 | Kunkel | 134/36 |

Primary Examiner—Ernest F. Karlsen
Assistant Examiner—Kevin D. O'Shea
Attorney, Agent, or Firm—Stephen A. Roen; Gerald R. Hibnick

[57] ABSTRACT

A method and apparatus for removing foreign matter, including debris and deposits and air bubbles from a flow cell of a particle study device. The apparatus includes a chamber with an aperture containing unit at one end and sample and sheath introduction mechanisms at the other end to supply respectively, a sample suspension of particles and a particle free liquid. The chamber has a waste orifice positionally disposed to provide a turbulent flow of particle free liquid within the chamber upon simultaneous injection and exhaustion of the particle free liquid into and out of, respectively, the sheath introduction mechanism and the waste orifice, to remove any air bubbles in the chamber and its adjacent aperture area. The debris and deposits are first removed, in a cross-chamber process and cross-aperture process, by injecting a mixture of gas and liquid into the chamber through a first orifice in both processes, to form droplets, and exhausting the mixture from a second orifice therein and through the aperture respectfully in each process. This foreign matter is further removed by another cross-aperture step, by injecting gas into the chamber through a first orifice and producing droplets and increasing its velocity via a waste orifice of the same chamber and exhausting the gas and droplets from a second orifice through the aperture. Then, the air bubbles are removed by injecting the particle free liquid into the flow cell to form the turbulent flow and then exhausting it.

34 Claims, 4 Drawing Figures

FIG-4.

METHOD AND APPARATUS FOR REMOVING FOREIGN MATTER FROM A FLOW CELL OF A PARTICLE STUDY DEVICE

BACKGROUND OF THE INVENTION

The invention relates generally to particle analyzing and/or studying apparatus having a flow cell with one or more chambers including an aperture containing means having an aperture for passage of fluid therethrough and through which particles in suspension are passed for study and more particularly to the removal of foreign matter, including debris and deposits and air bubbles, which if not so removed from the aperture and the area around it, part of its sensing zone, would effect the accuracy of the signals caused by the particles passing through the aperture. Furthermore, foreign matter from said fluid and particles may also accumulate and/or be left on or against the internal wall surfaces of said chambers and passageways leading to said aperture which if not removed could contaminate the chambers and/or serve as a source of said foreign matter which could eventually flow into the aperture sensing zone causing such accuracy problems. A potentially serious problem in this regard is a build up or presence of such foreign matter in the aperture itself, that is on its internal wall surfaces.

Since its conception in the early 1950's, the principle of particle counting and sizing invented by Wallace H. Coulter has resulted in numerous methods and flow-through apparatuses for the electronic counting, sizing, studying, and analysis of microscopic particles, which are scanned in a fluid suspension, as shown by the pioneer U.S. Pat. No. 2,656,508 to Coulter. In this prior art arrangement, a D.C. electric current flow is established between two vessels or chambers by suspending electrodes in the respective bodies or cavities of the suspension fluid. The only fluid connection between the two bodies is through an aperture; hence, an electric current flow and field are established in the aperture. The aperture and the resultant electric field in and around it constitute a sensing zone. As each particle passes through the sensing zone, for the duration of the passage, the impedance of the contents of the sensing zone will change, thereby modulating the current flow and electric field in the sensing zone, and causing the generation of a signal to be applied to a detector suitably arranged to respond to such change. (The mark "Coulter" is a registered trademark, Registration No. 995,825, of Coulter Electronics, Inc. of Hialeah, Fla.)

Systems are available for detecting and clearing the complete or substantially complete blockage of an aperture in particle study devices. One such circuit is shown and described in U.S. Pat. No. 3,259,891. This patent shows several debris clearing devices which require either complex mechanical linkages in order to mechanically remove the aperture debris or the actual removal of the aperture and/or aperture tube to manually remove the debris. The mechanical linkages are somewhat difficult to utilize and are cumbersome in operation. In the case of actually removing, cleaning and replacing an aperture tube, time is consumed which is to be avoided in operating the study devices, especially in structures with more than one aperture and furthermore this severly limits the throughput of the devices. Another debris clearing device shown in the patent employs a "burn circuit" which includes a capacitor charged to a high potential which is discharged via the electrodes creating a very high initial current flow through the aperture, thereby literally heating the contents of the aperture to explode and driving the obstruction out of the aperture. The rate of application of energy from the capacitor is not optimum or uniform and when sufficient energy is utilized to clear a blockage, it creates a serious threat of damage to the aperture material or aperture holding structure.

A second type of aperture clearing circuitry or burn circuit is shown in U.S. Pat. No. 3,963,984 which includes a pulse generator coupled to the electrode inside the aperture tube and to the electrode outside the particle tube in the fluid suspension. A pulse generator is coupled to the first and second electrodes and develops a combination of pulses having predetermined characteristics which are coupled to the electrodes and hence are coupled through the fluid contents of the aperture where they cause the fluid to vaporize and cause a microscopic explosion. Again, the force of the explosion is intended to be controlled to dislodge the debris without causing damage to the aperture or aperture structure; however, even at the optimum such an RF burst is highly energy wasteful. Furthermore, RF frequency applied to the aperture may cause a noise problem in the particle device itself. Further, it has been found that such a high frequency combination of pulses does not clean the internal surface of the aperture as completely as desired.

The particle signals may be significantly effected even though the aperture is not blocked. It is therefore useful to maintain the aperture as clean as possible without wasting energy, deteriorating the aperture structure and so that the aperture does not become increasingly smaller as a number of particle fluid samples is passed therethrough. Such cleaning is accomplished as described in the commonly assigned Canadian Pat. No. 1,163,294 of John Luscambe Martin, entitled "Aperture Cleaning System", by applying a substantially constant energy level for a predetermined period of time to the fluid in the aperture to boil the fluid therein thereby cleaning the aperture, that is cleaning the inner wall surfaces defining the aperture. The movement of fluid through the aperture may be stopped and a D.C. current applied during the rinse cycle of the devices between cycles of passing the particles in suspension through the aperture for optimum energy conservation. As described therein, the aperture will pass the particles in suspension therethrough for measuring. However, in examining white cells, the red cells are lysed and in doing so their structure is destroyed releasing their internal chemicals and protein into the suspension which then is passed through the aperture. The fluid of the suspension or electrolyte itself also contains chemicals and the protein and chemicals may build up on the internal surfaces of the aperture among other areas. As the build up increases, the size of the aperture decreases and hence the signal will vary although the same size particle has been passed therethrough each time. An ordinary rinse solution and rinsing would not eliminate this problem, hence the aforedescribed approach.

Gas bubbles, as previously indicated, are part of the foreign matter problem, and when they pass through or near the aperture and its sensing zone, they can produce erroneous particle counting and/or clogging of the aperture. One apparatus directed toward solving this problem is shown in U.S. Pat. No. 3,854,088, Counting and Analysis Apparatus for Particles Suspended in an Electrolytic Fluid, issued Dec. 10, 1974, to Gahwiler. It includes a direct-current supply electrode 11, arranged in the sample container 70, such that gas bubbles formed thereat do not reach the connection conduit 15, which is upstream of the sensing aperture 20, of the counting cell 1, and through which the sample flows. Another such apparatus is shown in U.S. Pat. No. 3,648,158, Conductivity Cell for Particle Counting, issued Mar. 7, 1972, to Parker. It includes a cell which comprises an upstream electrode 36, a sensing aperture 56, and a downstream electrode 38, within an output passageway 62, having a vent passage 72. Electrolysis resulting gas bubbles forming on the surface of the downstream electrode 38, are purged when outside air is drawn into the passageways, 61 and 62, via the vent port 74, causing purging of the system's fluid path, passageway 61 and 62, and its flow tube 16, of any remaining fluid and said gas bubbles after the completion of a counting run. Still another apparatus is shown in U.S. Pat. No. 3,781,675, Self Priming Conductivity Cell, issued Dec. 25, 1973, to Angel, wherein a priming or purging operation utilizing a bubble chamber is disclosed. Angel states:

"After an analytical run, the vent is opened to purge liquid from the cell, which eliminates conduction between the electrodes and which prepares the cell for a subsequent analytical run. (Col. 1, lines 42–52) During analysis of a particle-containing liquid, gas bubbles which can form on the electrode surfaces by reason of electrolysis or which may be present in the liquid sample can be drawn through the metering aperture to cause spurious sensing of gas bubbles as true particles and resulting in an erroneous count."

The patent's stated object is "to provide an improved conductivity cell in which bubbles within the cell do not materially affect system performance." Angel goes on to further explain that:

"During counting operation, gas bubbles which may form on the electrode surfaces or which may be present in a sample being analyzed are collected in a position within the cell removed from the aperture to prevent their flow through the aperture during analysis. After an analytical run, in which particles in a predetermined volume of liquid are counted, the cell is operated in a priming mode to remove gas bubbles and an analyzed liquid sample from the cell, and to infuse a new liquid sample for subsequent analysis. Cross-contamination of samples is eliminated by virtue of the priming operation since an old liquid sample within the cell is replaced with a new sample prior to a subsequent counting run.

During a portion of the priming operation, air is caused to flow through the aperture in a reverse direction to that of liquid flow during analysis, such air flow serving to backflush the aperture to clear any debris which can accumulate in or near the aperture during analysis." (Col. 1, line 67 to Col. 2, line 19)

Angel describes the operation of the bubble chamber as follows:

"Bubbles which tend to form during analytical run such as by electrolysis, or which are present in a liquid sample, rise to the top of chamber 76 away from the path of liquid flow and do not therefore interfere with the accuracy of the cell counting operation as no bubbles are drawn through the aperture 68." (Col. 5, lines 40–46)

He further describes in detail the operation of the preferred embodiment as follows:

"With the plunger in its depressed position, as depicted in FIG. 6, the channels 119 are in a position straddling the lower O-ring 117 to provide a path between passages 96 and 102 to cause purging of particle-containing liquid after an analytical run and priming of the cell for a succeeding run. During the initial period of a priming operation, vent 48 is closed and a vacuum on passage 102 provided by the system pump causes liquid in passages 74 and 76 to be drawn via passage 96 through channels 116 into passages 98 and 102, and thence to the waste bottle. Any residual liquid between the aperture 68 and the input passage is also drawn out through the purging path. Air bubbles collected in the upper portion of passage 96 are also withdrawn along with the liquid. The hydraulic impedance of the purging path is lower than that of the cell couting path, and thus, during purging, liquid flow tends to bypass aperture 68 and to flow into passage 96 for removal from the cell.

After purging of the liquid from the cell, vent 48 is opened and, with plunger 100 remaining depressed, air is drawn into the vent passage and through aperture 68 in a direction opposite to that of liquid flow during a counting run, and thence via passages 76, 96, channels 116 and passage 102 into the waste bottle. Air and bubbles within the flow tube 16 are also drawn into the waste bottle during this operating state. The reverse flow of air through aperture 68 causes backflushing of debris which can accumulate in the aperture, and, thus, the invention provides not only purging of the cell for a subsequent analytical run but also automatic cleaning of the aperture between runs." (Col. 5, line 53 to Col. 6, line 17)

SUMMARY OF THE INVENTION

The invention, in its broadest aspects, includes a particle analyzing apparatus and a method of removing gas bubbles therefrom as well as a method for removing foreign matter including debris and deposits from a flow cell of such an apparatus. The particle analyzing apparatus invention, in its broadest aspect, comprises a chamber, having a first end, for holding sample liquid suspension of particles to be analyzed, an output means having an end, and an aperture containing means having an aperture, said aperture means having a first end, disposed at the first end of said chamber and a second end disposed at said end of said output means. It further includes a sample means or introduction means having an outlet for supplying said sample liquid suspension of particles through said aperture of said aperture containing means and a sheath means for providing a particle free liquid passage to said chamber. The particles in suspension, when they pass through said aperture, pass through a sample flow path located between said outlet and said aperture. The chamber has a waste orifice provided therein which is positionally disposed in and near the flow path. A turbulent flow of particle free liquid is formed within said chamber in and near said waste orifice upon simultaneous injection of said particle free liquid at said sheath means for flow within said chamber and said first end of said aperture containing means, and exhaustion of said particle free liquid through said waste orifice, whereby any gas bubbles are removed from said chamber and/or said first end of said aperture containing means, through said waste orifice. The inventive method of removing gas bubbles from the apparatus, in its broadest aspect, comprises the steps of injecting a particle free liquid through a first orifice of said chamber, forming a turbulent flow of particle free liquid within said chamber in and near the flow path, and exhausting said turbulent flow of particle free liquid through a second orifice of said chamber, which second orifice is disposed near the flow path. One aspect of the inventive method of removing foreign matter, is to remove the same by a cross-chamber process, which, in its broadest aspect, includes, the steps of injecting a mixture of gas and liquid through the first orifice into said chamber to remove any foreign matter within said chamber, and exhausting said mixture and foreign matter through a second orifice. Another aspect of the inventive method of removing foreign matter, is to remove the same by a cross-aperture process, which, in its broadest aspect, includes the steps of injecting a mixture of gas and liquid through a first orifice into its chamber to clear debris primarily from said aperture, and clean deposits primarily from said aperture's walls, and exhausting said mixture and foreign matter through the aperture's other end. A further aspect of the inventive method of removing foreign matter, is to remove the same by another cross-aperture process, which, in its broadest aspect, includes the steps of injecting gas through a first orifice or port into its chamber to remove any foreign matter within said chamber, to clear debris from its aperture, and clean deposits from said aperture's wall, and exhausting said gas and foreign matter through the aperture's other end. In a narrower aspect thereof the injected gas has its velocity increased by differential pressure applied via another port or waste orifice of the same chamber. The invention, in another aspect, includes a method of removing foreign matter including debris, deposits, and gas bubbles from the flow cell of the particle analyzing apparatus by a series of substeps or combination of steps including removing the debris and deposits in a cross-chamber and two cross-aperture processes, respectively, and removing the air bubbles in another substep. Each of these four substeps are separately described supra.

DESCRIPTION OF THE PREFERRED EMBODIMENT

Figures 1, 2, 3:
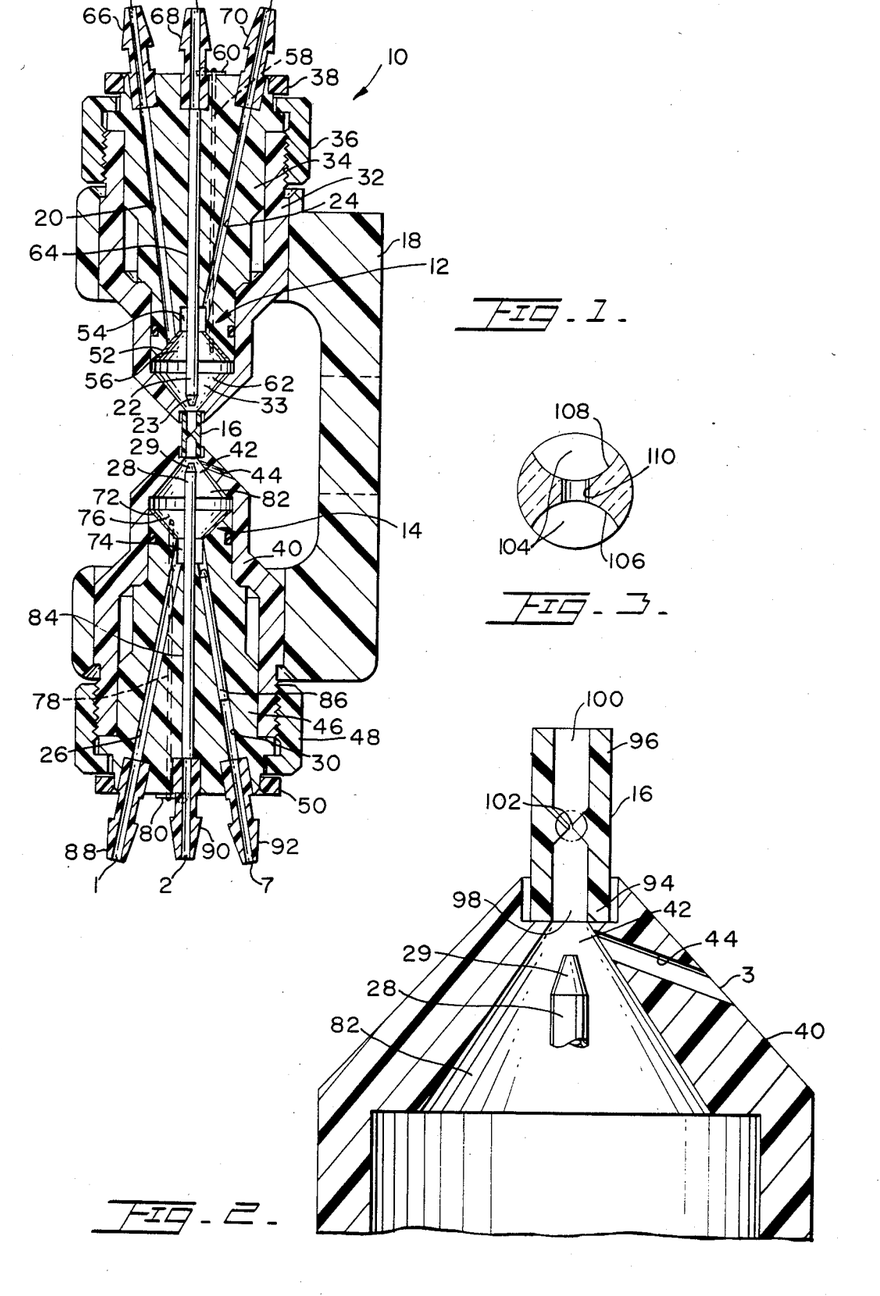
FIG. 1 is a cross-sectional view of the flow cell of the particle analyzing apparatus embodying the present invention.
FIG. 2 is an enlarged fragmentary cross-sectional view of a portion of FIG. 1 which includes its aperture containing means and a portion of the lower chamber with its side waste port.
FIG. 3 is an enlarged cross-sectional view of the sensing aperture region of the aperture containing means of FIG. 2.

Referring now to the drawings, particularly to FIGS. 1 and 2, a flow cell 10 of a particle analyzing or study apparatus or device comprises a first, upper, and second, lower, chamber generally indicated as 12 and 14, respectively, in fluid communication at their inner ends with a quartz aperture containing means 16, all of which are axially positionally aligned by a flow cell support means or yoke 18. Fluidly connected to said first chamber 12 is a sweep sheath passageway 20, a sample waste tube 22 having a tip 23, and an upper waste passageway 24. Fluidly connected to said second chamber 14 is a flush passageway 26, a sample introduction tube or means 28, and a sheath focus passageway or means 30. The first chamber or output means 12 comprises a generally conically shaped concentric, hollow, open ended upper body support member 32 including a lower end 33, which upper body support member 32 is disposed within and is adhesively secured to an upper end of yoke 18, a generally complementarily and conically shaped concentric upper body member 34 concentrically disposed within said upper body support member 32, an upper cap 36 which treadingly engages an upper portion of the upper body support 32 and which has an inwardly extending lip which engages an upper end of the upper body member 34 thereby securing the upper body member 34 to its upper support member 32, and an upper retainer ring 38 adhesively secured to the uppermost portion of upper body member 34. The second chamber 14 similarly comprises a generally complementarily and conically shaped concentric, hollow, open ended lower body support member 40 including a first end 42 at its upper end and having a side waste passageway 44 formed therein, which lower body support member 40 is disposed within and is adhesively secured to a lower end of yoke 18, a generally conically shaped concentric lower body member 46 concentrically disposed within said lower body support member 40, a lower cap 48 which threadingly engages a lower portion of the lower body support member 40 and which has an inwardly extending lip which engages a lower end of lower body member 46 thereby securing the lower body member 46 to its lower support member 40, and a lower retainer ring 50 adhesively secured to the lowermost portion of lower body member 46. The upper body member 34 of the first chamber 12 includes a lower end 52 which is generally conically shaped with its apex portion having a lower bore 54 axially extending a short distance therethrough. Mounted to the conically shaped portion of said lower end 52 is a mating downstream electrode 56 which is connected by a lead 58 to a first output terminal 60. A first or upper cavity 62 is defined by the lower surface of said downstream electrode 56 and the inner wall surfaces of said lower end 33 of said body support member 32. Three passageways axially extend through the upper end of said upper body member 34 to its lower end 52 and are in fluid communication with said upper cavity 62; a sample waste passageway 64 disposed at the axis and having said sample waste tube 22 disposed therein, the upper waste passageway 24 and sweep sheath passageway 20 both angularly positioned in surrounding coaxial relationship with said sample waste tube 22. These three passageways, sweep sheath, sample waste, and upper waste passageways, 20, 64, and 24, respectively, open, at their upper ends, to fittings 66, 68, and 70, respectively, through sweep sheath, sample waste, and upper waste ports, 6, 5, and 4, respectively. Similarly the lower body member 46 of the second chamber 14 includes an upper end 72 which is generally conically shaped with its apex portion having an upper bore 74 axially extending a short distance therethrough. Mounted to the conical portion of said upper end 72 is a mating upstream electrode 76 which is connected by a lead 78 to a second output terminal 80. A second or lower cavity 82 is defined by the upper surface of said upstream electrode 76 and the inner wall surfaces of said upper or first end 42 of said lower body support member 40. Three passageways axially extend through the lower end of said lower body member 46 to its upper end 72 and are in fluid communication with said lower cavity 82, a sample introduction passageway 84 disposed at the axis and axially aligned with its counter part the sample waste passageway 64 and having said sample introduction tube 28 disposed therein, the flush passageway 26 and sheath focus passageway 30, with a restriction means 86 disposed in the later, both passageways angularly positioned in surrounding coaxial relationship with said sample introduction tube 28. These three passageways, flush, sample introduction, and sheath focus passageways, 26, 84, and 30, respectively, open, at their lower ends, to fittings 88, 90, and 92, respectively, through flush, sample introduction, and sheath focus ports, 1, 2, and 7, respectively.

The restriction means 86 provides effective electrical isolation between the upstream electrode 76 and the sheath liquid source (not shown).

The aperture containing means 16 has formed therein at its lower end 94 and its upper end 96, a pair of opposed bores, lower bore 98 and upper bore 100, respectively, and walls which define a microscopic sensing aperture 102 which forms a fluid passageway between the inner ends of said opposed bores 98 and 100. The aperture containing means 16 is secured adhesively, at its lower and upper ends, 94 and 96, respectively, within the open ends, bores formed at the upper and lower ends, 42 and 33, respectively, of said lower and upper body support members, 40 and 32, respectively. A conventional sample flow path is located between said aperture 102 and the outlet of said sample introdcution tube 28.

The flow cell 10 is formed of transparent synthetic resin such as high impact polystyrene or other material which will not react with the reagents to which it will be exposed, except for the quartz aperture containing means 16, the borosilicate glass sample introduction and waste tubes, 28 and 22, respectively, and the aperture 102 itself.

Referring now specifically to FIG. 2, the side waste passageway 44 has a waste orifice or side waste port 3 which is in fluid communication with the lower cavity 82 and which is positionally disposed in said second chamber 14 near or in a region of turbulent, non-laminar, flow of particle free liquid formed within the lower cavity 82 of said second chamber 14 and in the bore 98 of the lower end 94 of said aperture containing means 16 upon, as explained in more detail hereinafter, by simultaneous injection of particle free liquid at said sheath focus passageway or means 30 through its sheath focus port 7 and/or, at said flush passageway 26 through its flush port 1, and exhaustion of the particle free liquid through the waste orifice 3, whereby any gas bubbles are removed from the lower cavity 82 of the second chamber 14 and/or from the bore 98 of the lower end 94 of the aperture containing means 16, through the waste orifice 3. Furthermore, the waste orifice 3 of the side waste passageway 44 is disposed as close as practically possible to the point where the flow of particle free liquid would deliver any gas bubbles to their natural point of accumulation in said cavity 82 and/or said bore 98 of said lower end 94. The natural point of accumulation of any such air bubbles in the preferred embodiment would be the uppermost point in one of the compartments, cavity 82 or bore 98, namely some point in the bore region 98. Practicality dictates however that the side waste passageway 44 be drilled or otherwise formed not in the quartz aperture element 16 but in the styrene lower body support 40.

Preferably, but not necessarily, the bores 98 and 100 of the aperture containing means 16 have a circular cross section of 0.05 inches with the overall length of the aperture containing means 16 being 0.25 inches. The aperture containing means 16 is formed from a monolithic piece of quartz, which permits it to be quite small. The smaller its size, the better its optical characteristics, in that the aperture containing means 16 approaches a point source for optical signals used therewith. The cross section of the particle sensing aperture 102 preferably approximates a square. As seen in this enlargement of FIG. 3, the ends of the bores 100 and 98, the mouths 104 of the aperture 102, are formed with spherical surfaces 106 and 108, which are each interrupted by the aperture 102. By providing rounded ends for the bores, the aperture 102 does not have to be precisely located. The outside surfaces are flat and parallel to walls 110 of the aperture 102. Typically, the aperture 102 has walls 110 with lengths of 50 to 100 micrometers. Preferably, the aperture 102, the exit and entrance orifices of the sample introduction and waste tubes 28 and 22, respectively, and the bores 100 and 98 are coaxially aligned. The above-described dimensions and configurations described in this paragraph are merely illustrative and can assume other shapes and sizes, respectively.

Aspiration and delivery of sample, through said flow cell 10 into a cell analyzing system for biomedical investigation, such as a COULTER ® EPICS ® V System, described in its product reference manual of February 1982, part number 4235066B, available from Coulter Electronics, Inc., Hialeah, Fla., is conventionally accomplished. Another operational cycle is initiated, namely RECYCLE, to return the flow cell 10 to its sample running mode as described in detail hereinafter, through the use of appropriate pneumatics and hydraulics under the control of a microprocessor (not shown), a method, in accordance with the instant invention, when required to remove all foreign matter including debris, deposits, and gas bubbles from said flow cell 10 so that sample can be properly run through said flow cell 10. (COULTER is the registered trademark no. 995,825 of Coulter Electronics, Inc., Hialeah, Fla., and EPICS is the registered trademark no. 1,175,973 of Coulter Corporation, Hialeah, Fla). RECYCLE can either be operator initated, as in the preferred embodiment or included within the system's program so as to be automatically performed under certain conditions. The full RECYCLE operational cycle is illustrated in tabular form hereinafter with execution times and includes six subroutines and/or modes of operation, FLUSH, PURGE, FILL, DEBUBBLE, PRIME and RUN, the later two which are completely conventional. The first three essentially remove debris and deposits, and the fourth essentially removes gas bubbles therein; the fifth step, PRIME, is a mode just prior to the actual sampling step the RUN mode, and is used to prime the flow cell 10 with the sample prior to said RUN mode during which time another sample is aspirated and delivered to the flow cell 10.

The preferred embodiment of operational cycle
RECYCLE

| SUBROUTINE | SUBSTEPS | TIME in Seconds |
|---|---|---|
| FLUSH | | |
| | FLBCA | 2 |
| | FLTCA | 2 |
| | FLBACK | 1 |

| SUBROUTINE | SUBSTEPS | TIME in Seconds |
|---|---|---|
| *-continued* | | |
| | FLFWRD | 1 |
| | FLBACK | 1 |
| | FLFWRD | 1 |
| | FLBACK | 1 |
| | FLFWRD | 1 |
| | FLBACK | 1 |
| | FLFWRD | 1 |
| PURGE | | |
| | PURGBC | 2 |
| | PURGTC | 2 |
| FILL | | |
| | FLBCAL | 2 |
| | FLTCAL | 2 |
| DEBUBBLE | | |
| | DEBUBL | 1 |
| | FLTCAL | 1 |
| | SHEATH | 1 |
| | DEBUBL | 1 |
| | FLTCAL | 1 |
| | SHEATH | 1 |
| | DEBUBL | 1 |
| | FLTCAL | 1 |
| PRIME | | |
| | SMPRMF | 1 |
| RUN | | |
| | RUN | → |

The DEBUBL subroutine itself consists of a pair of steps DEBUB 1 and DEBUB 2, repeated eight times, each step lasting 1/16 of a second. This subroutine can also be separately operator initiated when desired.

Figure 4:
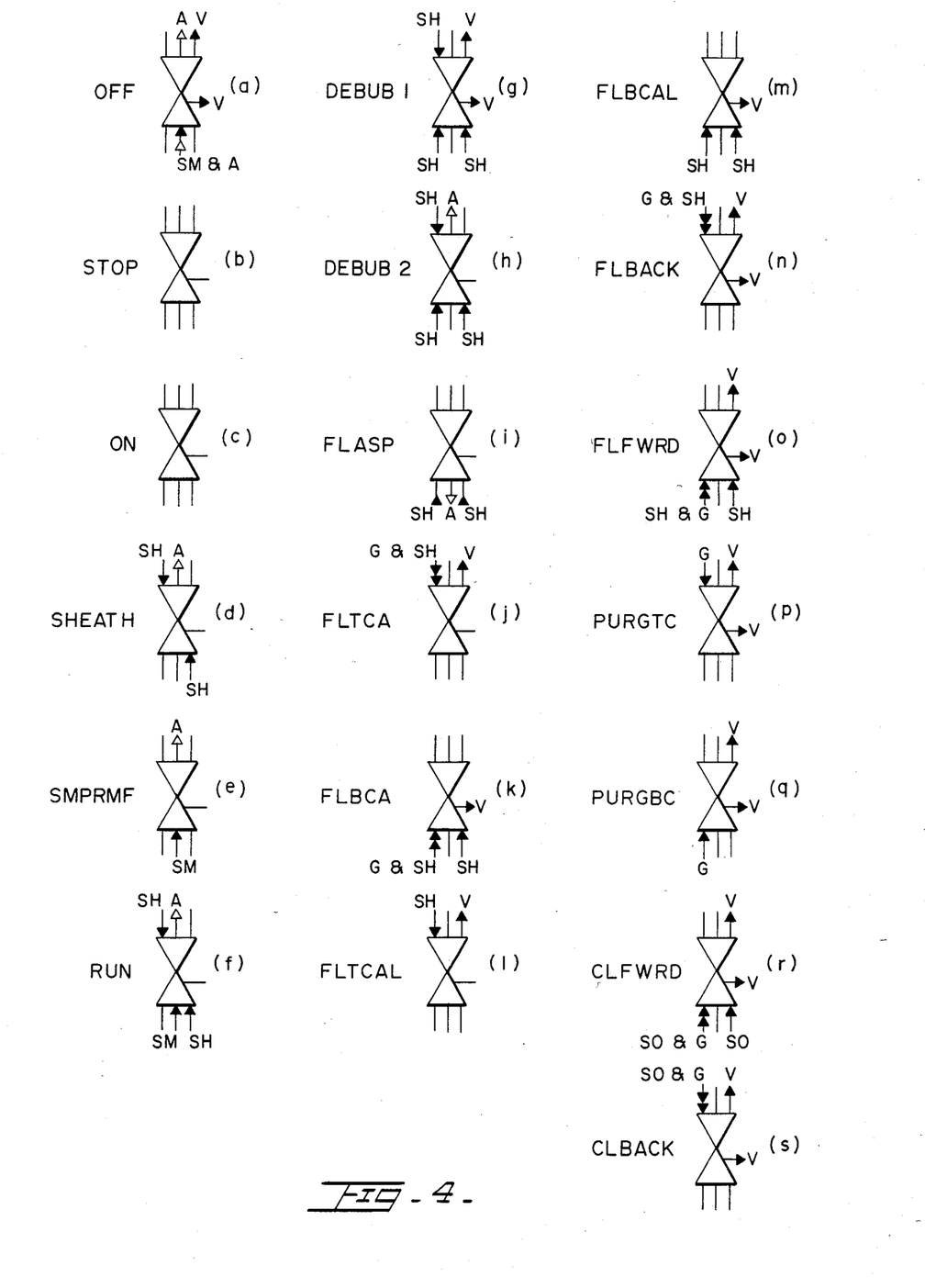
FIG. 4 is a series of schematic diagrams illustrating the various process states embodying the methods of the invention.

Referring now specifically to FIG. 4, a series of schematic drawings are shown which illustrate the various process states embodying the methods of the invention; and wherein solid arrows indicates injection and/or exhaustion at a positive or negative pressure, respectively, with respect to atmospheric pressure at the port to which it is applied and/or exhausted, wherein an open arrow indicates that the port to which it is applied to is simultaneously open to atmosphere, wherein two arrows at the same port indicate that two inputs are applied at the same time through a common port and wherein all injections and/or exhaustions occur simultaneously. Furthermore, the following legend key indicates the symbol meaning used therein;

A: AIR
G: GAS
SH: SHEATH
SM: SAMPLE
SO: SOAP
V: VACUUM

The FLUSH subroutine of the operational cycle RECYCLE sequence begins with one of the two cross-chamber foreign matter removal substep FLBCA as shown in FIG. 4 (k) to flush across the bottom or second chamber 14 and comprises injecting a mixture of nitrogen gas and sheath liquid through flush port or first orifice 1 and simultaneously injecting additional sheath liquid through sheath focus port 7 into its cavity 82 and exhasuting said mixture and any foreign matter through side waste port or second orifice 3 to waste, a waste accumulator (not shown), by application of a negative pressure or vacuum thereto. Then the other cross-chamber foreign matter removal substep, FLTCA, as shown in FIG. 4 (j) begins to flush across the top or first chamber 12 and comprises injecting this mixture of the nitrogen gas and sheath liquid through sweep sheath port or first orifice 6 into its cavity 62 and exhausting said mixture and any foreign matter through upper waste port or second or waste orifice 4 to waste. These cross-chamber foreign removal steps remove any foreign matter generally within the two chambers 12 and 14 and more particularly clean deposits primarily from the walls of these chambers which define their cavities 62 and 82 and further clear debris away from their aperture 102 and primarily away from its mouths 104. Then a cross-aperture series of "toggling" steps are performed to primarily remove foreign matter from the aperture and begins with substep FLBACK as shown in FIG. 4 (n) to clear the aperture 102 in the reverse direction, that is in the direction opposite to the flow of sample through the aperture 102, and comprises injecting the mixture of nitrogen gas and sheath liquid through sweep sheath port 6 into the upper chamber's cavity 62 and exhausting the mixture and the any foreign matter through the upper chamber's upper waste port 4 and the aperture's lower, and in this case its second and distal end 94 and then through the lower chamber's side waste port 3 to waste, by simultaneous application of a vacuum to said ports. Then essentially the same process is repeated in the opposite, forward, direction to clear the aperture 102 in the other direction by substep FLFWRD as shown in FIG. 4 (o) and comprises injecting the mixture of nitrogen gas and sheath liquid through flush port 1 and simultaneously injecting additional sheath liquid through sheath focus port 7 into the lower chamber's cavity 82 and exhausting the mixture and any foreign matter through the lower chamber's side waste port 3 and the aperture's upper, and in this case its second and distal end 96 and then through the upper chamber's upper waste port 4 to waste, by simultaneous application of a vacuum to said ports. These two substeps FLBACK and FLFWRD continue to alternately be performed as described previously, another three times. These series of cross-aperture foreign matter removing steps clear debris primarily from the aperture 102 and clean deposits primarily from said aperture's walls 110. The application of the vacuum, to a port in the chamber in which the mixture of nitrogen and sheath liquid is injected, results in providing a second acceleration to the injected mixture or jet, effectively increasing its velocity so that when said jet approaches the sensing aperture's mouth 104 its velocity is high enough to enable it to traverse the aperture 102 itself and to both clear debris from the aperture 102 and clean deposits from its walls 110. Without the application of the vacuum to the port in the chamber in which the mixture is injected the jet's velocity would be too low and therefore would not provide effective cleaning and clearing to the sensing aperture 102.

Utilization of the nitrogen gas and sheath liquid mixture together with its exhaustion as described hereinabove with respect to the FLUSH subroutine produces a particularly effective foreign matter removing process both as regards cleaning deposits and clearing debris. The gas and sheath liquid are injected at their common port at approximately the same pressures. However, the gas's velocity will be much greater than the fluid's velocity within their common passageway; that is the liquid within the common passageway will be accelerated to a higher velocity to form small liquid particles or a flow of droplets therein which droplets are entrained in the liquid-gas mixture in the common passageway and which particles gain momentum and increase their kinetic energy, thereby eliminating damping effects which otherwise would be caused by a flow of liquid into the chamber, in constrast to the flow of said droplets into said chamber. As a result of this initial or first acceleration of the liquid, the flow of liquid and gas will continue to breakup into small particles or droplets as or when it enters the chamber's cavity. These droplets, as they enter the chamber as part of the jet, will bombard, without any said damping effects to interfere, the walls of the cavity and the bore of the chamber where it is injected into, as well as the sensing aperture 102 itself in the case of the cross-aperture series of toggling steps which will provide the second acceleration effect, and together with a gas penetration action, which easily penetrates between deposits or debris and the surface against which they reside, the inner wall surfaces of said cavity and bore, and the sensing aperture 102 during the toggling steps, will erode and remove any deposits thereon or debris there against. This action is coupled with a turbulent type of flow in the lower cavity 82 whenever the process involves injection into the lower cavity 82 and evacuation through the side waste port 3, that is during the FLBCA and FLFWRD substeps.

Then the next sequential subroutine, PURGE, is performed, to purge, with the nitrogen gas, the chambers 12 and 14, and their common aperture 102, in opposite directions, to remove any further remaining debris and deposits. It begins with substep PURGBC as shown in FIG. 4 (q) and comprises injecting nitrogen gas through flush port 1 and exhausting the gas and any resulting, entrained, foreign matter through the lower chamber's side waste port 3 and the aperture's upper end 96 and then through the upper chamber's upper waste port 4 to waste, by simultaneous application of a vacuum to said ports. Then essentially the same process is repeated in the opposite, reverse, direction by substep PURGTC as shown in FIG. 4 (p) and comprises injecting nitrogen gas through sweep sheath port 6 and exhausting the gas and any resulting, entrained, foreign matter through the upper chamber's upper waste port 4 and the aperture's lower end 94 and then through the lower chamber's side waste port 3 to waste, by simultaneous application of a vacuum to said ports. The application of the vacuum, to a port in the chamber in which the nitrogen gas is injected, increases the velocity of the incoming gas and any produced droplets described hereinafter, so that when it, the gas and droplets, approaches the sensing aperture's mouth 104 its velocity is high enough to enable it to traverse and penetrate the aperture 102 itself, in the same manner as described with reference to the second acceleration effect of the prior performed cross-aperture foreign removing substeps which include such velocity increasing mechanism.

Additional cleaning and clearing is achieved by the PURGE subroutine which utilizes injection of nitrogen gas into one chamber and its exhaustion out of both chambers. This is due to its high pressure injection into the flow cell 10 which has its cavities or voids substantially completely evacuated of any sheath liquid remaining therein except for some residual liquid due to surface tension effects. The result is the elimination of liquid damping effects and the mixing of such residual liquid with said gas thereby producing, it is believed, an "ejection" action which includes an acceleration of small particles of liquid from said residual liquid due to such gas injection. These small particles of liquid produced are accelerated to a velocity far greater than they would be if they were injected alone into a passageway, and bombard the walls of the cavity and bore of the chamber where they are produced or ejected from as well as bombard the entrace of the sensing aperture 102. Additionally a gas penetration action easily penetrates through the smallest crevices between deposits or debris and the surface against which they reside, at said sensing aperture 102 and against the wall surfaces of said cavity and bore, and erodes and/or removes any deposits thereon or debris there against.

The third subroutine, FILL, is then performed to remove, with a flow of sheath liquid, any possible remaining foreign matter from both chamber 12 and 14. Substep FLBCAL is first performed, as shown in FIG. 4 (m) and comprises simultaneous injection of sheath liquid through flush port 1 and sheath focus port 7 and simultaneously exhausting the liquid and any foreign matter therein through the side waste port 3 to waste by application of a vacuum thereto. Then essentially the same process is repeated in the other chamber 12 by substep FLTCAL as shown in FIG. 4 (l) and comprises injection of sheath liquid through sweep sheath port 6 and exhausting the liquid and any foreign matter therein through upper waste port 4 to waste by application of a vacuum thereto.

The next subroutine, DEBUBBLE, which can also be separately performed by operator initiation, functions to essentially remove, with the flow of sheath liquid any gas bubbles present in the flow cell 10, and begins with substep DEBUBL which itself consists of a pair of steps DEBUB 1 and DEBUB 2, repeated a total of eight times, each separate step or execution time lasting a 1/16 of a second, for a total elapsed time of one second. DEBUB 1 essentially functions to remove any air bubbles, particularly large air bubbles, within either of the lower or upper chamber's cavities 82 and 62, respectively, and from the lower and upper bores 98 and 100, respectively, of the aperture containing means 16 and connecting lines (not shown). Substep DEBUB 1, as shown in FIG. 4 (g) comprises simultaneous injection at a positive pressure of a particle free liquid, sheath liquid, through at least one port of the lowest chamber, and in the preferred embodiment two ports thereof, flush port 1 and sheath focus port 7 of the lower or second chamber 14 and simultaneously exhausting the liquid and air bubbles trapped therein through the side waste port or second orifice 3 of said chamber to waste by simultaneous application of a negative pressure or vacuum thereto. The side waste passageway 3 is positionally disposed in such a relationship to the lower chamber 14 and its constituent parts as well as with respect to the aperture containing means 16 and its constituent parts so as to be near or in a region of non-laminar, turbulent flow of particle free liquid within the lower cavity 82 and/or the bore 98, formed when or upon simultaneous injection of said sheath liquid through said sheath means or sheath focus passageway 30 through its sheath focus port 7 and/or, at said flush passageway 26 through its flush port 1 and exhaustion of the sheath liquid through the waste orifice or port 3, whereby any gas bubbles present within the lower cavity 82 and/or the bore 98 are removed through this side waste orifice 3. This turbulent type of flow is caused, at least in part, by subsequently, changing, the direction of flow of the injected sheath liquid from its initial flow direction which, initially is the direction of the flow of liquid just as it exits from the flush port 1 and sheath focus port 7 of their passageways, flush passageway 26 and sheath focus passageway 30, respectively, and enters the lower cavity 14. As explained hereinbefore, air bubbles in the lower chamber, chamber 14, will tend to flow upwards toward the sensing orifice 102. Some of them, particularly if they are small enough will flow through the sensing aperture 102. Others which have not passed through the sensing aperture 102 may congest or become trapped in or at some or all the corner areas particularly in the areas near its lower mouth 104 including against the side surfaces defining the lower bore 98 and those air bubbles cause undesirable electrical noise when they vibrate if they are near the sensing zone or orifice 102. Others may congest in areas in the upper portion of the lower chamber and near tip 29 of the sample introduction tube 28 and particularly against the chamber's inner wall surfaces in said areas. In certain situations, relatively large air bubbles are generated and situate themselves between the lower chamber's inner wall surfaces and the introduction tube's tip 29. They tend to remain stationary against such surfaces and are difficult to remove therefrom due to the very high surface tensions created therebetween. By positioning the side waste passageway 44 in its relative position with respect to an injecting passageway or sheath means, previously described, the turbulent flow created by injection of sheath liquid at the lower end of the lower chamber 14 and sideway exhaustion of the turbulent flow through such side waste passageway 44 located which is near or in a region of turbulent flow and in the path of natural flow for air bubbles, that is a flow of air bubbles from a lower elevation to a higher elevation, is sufficient to and capable of clearing and carrying away, respectively, by exhausting through this side waste passageway 44 all such air bubbles from wherever they may accumulate in the lower half of said flow cell 10 as a result of this turbulent flow of sheath fluid within and around the entire volume of said cavity 82 and bore 98 and, in particular, as a result of the existance of the turbulent flow at the critical wall surfaces or boundaries thereof, including such flow past the critical outer wall surfaces or boundaries of the sample introduction tube's tip 29. Laminar flow, which has zero velocity at its boundaries, would not provide as effective air bubbles elimination at these critical wall surfaces. The preferred embodiment of the invention which is part of this substep further includes simultaneous injection of sheath liquid in said upper chamber 12 through sweep sheath port 6 and simultaneously exhausting the liquid and any air bubbles trapped therein through the upper waste port 4 to waste by simultaneous application of a vacuum thereto. The operations in each of the chambers, the lower and upper chamber 14 and 12, respectively, to remove air bubbles therein, particularly the larger air bubbles, take place in effective isolation from each other, as if the operations on each chamber were performed sequentially rather than simultaneously. DEBUB 2, the next substep performed, as shown in FIG. 4 (h), comprises simultaneous injection of sheath liquid through flush port 1 and sheath focus port 7 of the lower chamber 14 as well as through sweep sheath port 6 of the upper chamber 12 and exhausting, through hydrodynamic focusing, the sheath and any air bubbles, particularly smaller air bubbles trapped in the areas near the aperture's lower mouth 104 through sample waste port 5 to waste, both of which are open to air, and results in an increase in pressure in both chambers 12 and 14 as compared to the pressures created in these chambers during the DEBUB 1 substep. Substep FLTCAL is then performed as shown in FIG. 4 (l) and as described hereinbefore and functions, at this step in this process, to accelerate the movement of any remaining air bubbles in its upper chamber 12 and to remove them by application of the vacuum to the exhausting port, upper waste port 4. The substep SHEATH is then performed as shown in FIG. 4 (d) to further remove any remaining air bubbles in either chamber 12 or 14 and comprises simultaneous injection of sheath liquid through sheath focus port 7 and sweep sheath port 6 and exhausting the liquid and any such air bubbles in their cavities 12 and 14, respectively, through sample waste port 5 to waste, wherein the waste and the port through which the waste contents flow are open to air, that is they are both aat atmospheric pressure. These three substeps, DEBUBL, FLTCAL, and SHEATH are again repeated and thereafter the first two substeps, DEBUBL and FLTCAL, are further repeated to end the subroutine, all with a view toward removing any possibly remaining air bubbles in the flow cell 10. At the conclusion of this subroutine essentially all air bubbles, as described in more detail hereinafter, are removed from the area near the sensing orifice 102, within the lower bore 98 of the aperture containing means 16, between introduction tube's tip 29 and the adjacent lower chamber's inner wall surfaces, and any other corner areas.

Conventional subroutine PRIME is then performed which consists of a single substep, SMPRMF, and is performed directly before the actual sample run, the RUN mode, and functions to prime the flow cell 10 with the sample. Substep SMPRMF, as shown in FIG. 4 (e), comprises injecting the liquid sample to be run through the sample introduction port 2 into its introduction tube 28 within the lower chamber 14, which flow subsequently passes through the aperture 102 and into the sample waste tube 22 within the upper chamber 12 and out to waste through its port, sample waste port 5, the later two which are open to air.

Upon completion of the short, one-eighth of a second, PRIME subroutine, the RUN subroutine begins, for the requisite period of time, as shown in FIG. 4 (f), and comprises the injection of sheath liquid through both sheath focus port 7 and sweep sheath port 6 in their respective chambers 14 and 12 while continuing to maintain the flow of sample through sample introduction port 2 and exhausting both sample and sheath liquid present in the upper chamber 12 through the sample waste tube 22 and out to waste through its sample waste port 5 which remains open to air, all of which is conventionally performed in the flow cell 10 and accordingly not described in any further detail.

Two substeps, CLBACK and CLFWRD, not previously described are preferrably performed at the end of the day or whenever desired by the operator. These substeps, CLBACK and CLFWRD, utilize a mixture of gas and soap (detergent), in both the reverse and forward directions, to provide a heavy duty cleaning of the flow cell 10 which includes such cleaning of its chamber 12 and 14 and their cavities 62 and 82, respectively, as well as its aperture 102, and all other surfaces which define said cavities 62 and 82 and the bores 98 and 100 of the aperture containing means 16. Substep CLBACK as shown in FIG. 4 (s) comprises the injection of a mixture of nitrogen gas and soap through sweep sheath port 6 into the upper chamber's cavity 62 and exhausting the mixture and any foreign matter through upper waste port 4 and the lower chamber's side waste port 3 to waste, by simultaneous application of a vacuum to said ports. Then essentially the same process is repeated in the forward direction by substep CLFWRD as shown in FIG. 4 (r) and comprises an injection of the mixture of the gas and soap through flush port 1 and the injection of soap through sheath focus port 7, all into the lower chamber's cavity 82, and exhausting the mixture and any foreign matter through side waste port 3 and upper waste port 4 to waste, by simultaneous application of a vacuum to said ports. Thereafter, and at least at the end of the day, subroutine STOP is performed as shown in FIG. 4 (B) resulting in all the ports being closed. If the flow cell 10 is deactivated, as for example when the particle study apparatus is turned off, subroutine OFF is performed as shown in FIG. 4 (a) and comprises, depending on the position of the aspirator (not shown), the injection of remaining sample into the sample introduction port 2 when the aspirator is in a down position within a sample tube or other container or the entry of air into the sample introduction port 2 when the aspirator is in an up position out of the sample container and exposed to atmospheric pressure or air, and exhausting either the sample and/or air, for a sufficient period of time to purge both chambers 14 and 12 of any such sample by exhausting it through side waste port 3 and upper waste port 4 to waste, by simultaneous application of a vacuum to said ports while opening the sample waste port 5 to air. When the flow cell is turned on, as for example when the particle study apparatus is turned on, subroutine ON as shown in FIG. 4 (c) is initiated, all the ports being closed and the clock of the microprocessor is turned on to provide the proper execution times for the various routines, subroutines, substeps, etc. When it is desired or commanded, the aspirator is back flushed through subroutine FLASP as shown in FIG. 4 (i) and comprises the injection of sheath fluid through flush port 1 and sheath focus port 7 of the lower chamber 14 and exhausting this liquid through the sample introduction port 2 through its tube 28 to the aspirator through a series connected sample line (not shown), which aspirator and the port through which the sheath liquid flows is open to air, at atmospheric pressure.

The operative parameters of the preferred embodiment are as follows, dimensions given in inches:

| PASSAGEWAY DIAMETERS | | |
|---|---|---|
| Flush (1) Passageway (26) 0.45 | Side (3) Passageway (44) .030 | Upper (4) Passageway (24) .045 |
| Sweep (6) Passageway (20) .045 | | Focus (7) Passageway (30) .045 |

The vacuum at the vacuum pump (not shown) is approximately −11 PSI, the sheath fluid is pressurized to 8 P.S.I. and 5 P.S.I. at the lower and upper chambers, respectfully, the nitrogen gas is pressurized to 10 P.S.I. and the soap is pressurized to 9 P.S.I. The preferred embodiment of the invention utilizes ISOTON ® liquid for the sheath fluid and ISOTERGE ® liquid for the soap detergent used. (ISOTON ® and ISOTERGE ® are registered trademarks No. 848,055 and 859,453, respectively, of Coulter Electronics, Inc., Hialeah, Fla.)

The sensing aperture 102 not only serves as an electronic volume sensing zone, according to the principle of Wallace Coulter, as will be described below but also serves as an optical sensing zone. A low frequency current (including D.C.) or high frequency current source (not shown) or both is electrically coupled to the electrodes 56 and 76 by way of electrical conductors 58 and 78, respectively. As the particles pass through the aperture 102, they modulate the electrical current so as to produce particle pulses detected by conventional detector circuitry (not shown). Illustrative current sources and detection circuitry are shown in U.S. Pat. Nos. 3,710,933; 3,502,974 and 3,502,973, which are incorporated herein by reference.

Although the apparatus is used primarily for studying cells, it is equally applicable to kinds of particles.

Although particular embodiments of the invention have been shown and described herein, there is no intention thereby to limit the invention to the details of such embodiments. On the contrary, intention is to cover all modifications, alternatives, embodiments, usages and equivalents of the subject invention as fall within the spirit and scope of the invention, specification and the appended claims. For example, there is a certain amount of interchangeability between the ports, that is the upper waste port 4 could be used as the entry port instead of the sweep sheath port 6, and the flush port 1 could be used instead of the sheath focus port 7 and vice versa, with attendant addition and/or elimination of the restriction means in the appropriate passageway. Furthermore, although liquid and/or gas are indicated as being injected at a positive pressure through one port and removed or exhausted through another port by a negative pressure, a vacuum, all that is required is that a differential pressure of the appropriate magnitude be applied across these ports. For example the invention is intended to encompass the drawing, as an injection, into the chamber through one port of the chamber of a gas and/or a liquid, by the application of a vacuum at another port in the chamber or flow cell.

What is claimed is:

1. A method of removing gas bubbles from a flow cell of a particle study device, said flow cell comprising: at least one chamber, said chamber having a first and a second orifice; a particle introduction means disposed within said chamber, said particle introduction means having an outlet; an aperture means having an aperture, said aperture means being connected to said chamber; a flow path located between said outlet and said aperture; particles in suspension being capable of passing through said aperture and through said flow path for particle study; said method comprising:
    injecting a particle free liquid through said first orifice of said chamber, to form a turbulent flow of particle free liquid within said chamber in and near said flow path, and
    exhausting said turbulent flow of particle free liquid through said second orifice of said chamber, at a point near said flow path.

2. The method as recited in claim 1, wherein said steps of injecting and exhausting are provided by applying a differential pressure across said first and second orifices.

3. The method as recited in claim 2, wherein said step of exhausting said turbulent flow of particle free liquid through said second orifice is provided by applying a negative pressure thereto.

4. The method as recited in claim 3, wherein said step of injecting a particle free liquid through said first orifice is provided by injecting said liquid at a positive pressure.

5. The method as recited in claim 1, wherein said forming of said turbulent flow is provided by subsequently changing the direction of flow of said injected particle free liquid from its initial flow direction.

6. The method as recited in claim 1, wherein said flow cell comprises two chambers, a first chamber and second chamber, and wherein said first chamber is disposed above said second chamber, and wherein said turbulent flow of particle free liquid is formed within said second chamber, further comprising the steps of:
   injecting a particle free liquid through said first orifice of said first chamber, and
   exhausting said flow of particle free liquid through said second orifice of said first chamber.

7. A method of removing foreign matter including debris and deposits from a flow cell of a particle study device, said flow cell comprising: at least one chamber, said chamber having an inner end and a first orifice; and an aperture means having walls which define an aperture, said aperture means having a first end connected to said inner end of said chamber and a second end disposed distally from said chamber; particles in suspension being capable of passing through said aperture for particle study; said method comprising:
   injecting a mixture of gas and liquid through said first orifice into said one chamber to:
      clear debris primarily from said aperture, and
      clean deposits primarily from said walls which define said aperture, and
   exhausting said mixture and foreign matter through said second end of said aperture means.

8. The method as recited in claim 7, wherein said flow cell comprises two chambers, a first and second, and wherein both said steps of injecting and exhausting are performed alternately between said first and second chambers.

9. The method as recited in claim 8, wherein said first chamber is disposed above said second chamber, and wherein said alternation begins with said second chamber.

10. The method as recited in claim 7, wherein said one chamber includes a waste orifice and wherein said exhausting is accomplished through said second end of said aperture means and through said waste orifice.

11. The method as recited in claim 10, wherein said exhausting is accomplished simultaneously through said second end of said aperture means and through said waste orifice.

12. The method as recited in claim 7, wherein said mixture of gas and liquid forms droplets which enter said one chamber.

13. A method of removing foreign matter including debris and deposits from a flow cell of a particle study device, said flow cell comprising: at least one chamber which has a first orifice and a waste orifice; and an aperture means having walls which define an aperture, said aperture means having a first end connected to said chamber and a second end disposed distally from said chamber; particles in suspension being capable of passing through said aperture for particle study; said method comprising:
   injecting gas through said first orifice into said one chamber to:
      remove any foreign matter within said one chamber,
      clear debris from said aperture, and
      clean deposits from said walls which define said aperture, and
   exhausting said gas and foreign matter through said second end of said aperture means and through said waste orifice.

14. The method as recited in claim 13, wherein said flow cell comprises two chambers, a first and second, and wherein both said steps of injecting and exhausting are performed alternately between said first and second chambers.

15. The method as recited in claim 14, wherein said first chamber is disposed above said second chamber, and wherein said alternation begins with said second chamber.

16. The method as recited in claim 13, wherein exhausting is accomplished simultaneously through said second end of said aperture means and through said waste orifice.

17. The method as recited in claim 13, wherein said gas when injected into said chamber produce droplets from any residual liquid therein.

18. A method of removing foreign matter including debris, deposits, and gas bubbles from a flow cell of a particle study device, said flow cell comprising: at least one chamber, said chamber having a first orifice and a second orifice; an aperture means having walls which define an aperture, said aperture means having a first end connected to said chamber and a second end disposed distally from said chamber; particles in suspension being capable of passing through said aperture for particle study; said method comprising:
   (A) cross-chamber foreign matter removing steps comprising:
      injecting a mixture of gas and liquid through said first orifice into said one chamber to remove any foreign matter within said one chamber, and
      exhausting said mixture and foreign matter through said second orifice,
   (B) first cross-aperture foreign matter removing steps comprising:
      injecting a mixture of gas and liquid through said first orifice into said one chamber to:
         (a) clear debris primarily from said aperture, and
         (b) clean deposits primarily from said walls of said aperture means, and
      exhausting said mixture and foreign matter through said second end of said aperture means, and
   (c) second cross-aperture foreign matter removing steps comprising:
      injecting gas through said first orifice into said one chamber to:
         (a) remove any foreign matter within said chamber,
         (b) clear debris from said aperture, and
         (c) clean deposits from said walls of said aperture means, and
      exhausting said gas and foreign matter through said second end of said aperture means,
   (D) cross-chamber and past aperture gas bubble removing steps comprising:
      injecting a particle free liquid through said first orifice of said chamber,
      forming a turbulent flow of particle free liquid within said chamber, and
      exhausting said turbulent flow of particle free liquid through said second orifice.

19. A method of removing gas bubbles from a flow cell of a particle study device, said flow cell comprising: first and second chambers; said first chamber being an upper chamber and having a first orifice and a waste orifice; said second chamber having a first orifice and a second orifice; each of said chambers having an inner end; an aperture means having an aperture, said aperture means being connected to said inner ends of said chambers; particles in suspension being capable of passing through said aperture; said method comprising:

injecting particle free liquid through said first orifice of said first chamber, and     injecting, simultaneously, particle free liquid through said first orifice of said second chamber.

20. The method as recited in claim 19, including pressurizing said chambers by performing said fluid injecting under pressure.

21. The method as recited in claim 20, further comprising simultaneously exhausting said fluid and any gas bubbles within said chambers through said waste orifice of said first chamber.

22. The method as recited in claim 19, wherein said waste orifice of said first chamber is open to atmospheric pressure.

23. In a method of removing foreign matter including debris and deposits from a flow cell of a particle study device, said flow cell comprising: at least one chamber, said chamber having a first orifice, a second orifice, and inner wall surfaces; a particle introduction means disposed within said chamber, said particle introduction means having an outlet; an aperture means having an aperture with a mouth, said aperture means being connected to said chamber; a flow path located between said outlet and said aperture; particles in suspension being capable of passing through said aperture and through said flow path for particle study; said method comprising:

deriving a mixture of gas and liquid from separate sources, and     introducing said mixture into said chamber to remove any foreign matter within said chamber.

24. In the method as recited in claim 23, causing said chamber to be substantially free of any liquid during said introducing of said mixture.

25. In the method as recited in claim 23, causing said mixture to be under sufficient pressure and in amounts sufficient to form droplets.

26. In the method as recited in claim 25, wherein said introducing is by injecting under pressure said mixture into said chamber.

27. In the method as recited in claim 26, causing, by said injecting, said droplets to impinge against said inner wall surfaces of said chamber.

28. In the method as recited in claim 27, cleaning deposits primarily from the walls of said chamber by said injecting.

29. In the method as recited in claim 27, further including exhausting said mixture out of said chamber.

30. In the method as recited in claim 29, wherein said injecting and exhausting are provided by applying a differential pressure across said chamber.

31. In the method as recited in claim 29, clearing debris away from said aperture and primarily away from said mouth of said aperture by said injecting.

32. A flow cell of a particle analyzing apparatus, said flow cell comprising:

(A) a chamber having a first end for holding sample liquid suspension of particles to be analyzed;

(B) output means having an end;

(C) an aperture containing means having a first end, disposed at said first end of said chamber, and a second end disposed at said end of said output means;

(D) sample means for supplying a sample liquid suspension of particles through said first end of said aperture containing means; and     (E) injection means for providing a passage to inject a particle free liquid into said chamber for forming a region of turbulent flow of particle free liquid within said chamber;

said chamber having a waste orifice which is disposed near or in said region of turbulent flow for exhausting the flow of particle free liquid from within said chamber through said waste orifice, whereby any foreign matter is removed from said chamber and/or said first end of said aperture containing means.

33. The apparatus as recited in claim 32, wherein said waste orifice also is disposed as close as possible to a point where the flow of particle free liquid would deliver any gas bubbles to their natural point of accumulation in said chamber.

34. The apparatus as recited in claim 32, wherein said injection means and said waste orifice are disposed on opposite sides of said chamber.

* * * * *